(12) United States Patent
Miser

(10) Patent No.: US 6,733,514 B2
(45) Date of Patent: May 11, 2004

(54) JAW ASSEMBLY FOR ENDOSCOPIC INSTRUMENTS

(75) Inventor: John D. Miser, Apex, NC (US)

(73) Assignee: Pilling Weck Incorporated, Limerick, PA (US)

( * ) Notice: Subject to any disclaimer, the term of this patent is extended or adjusted under 35 U.S.C. 154(b) by 32 days.

(21) Appl. No.: 09/971,913

(22) Filed: Oct. 5, 2001

(65) Prior Publication Data

US 2003/0069598 A1 Apr. 10, 2003

(51) Int. Cl.[7] ............................................. A61B 17/28
(52) U.S. Cl. ...................................... 606/206; 606/208
(58) Field of Search ................................ 606/205–210, 606/170, 119, 120

(56) References Cited

U.S. PATENT DOCUMENTS

| | | | |
|---|---|---|---|
| 5,431,675 A | * | 7/1995 | Nicholas et al. ............ 606/206 |
| 5,556,416 A | | 9/1996 | Clark et al. |
| 5,766,205 A | * | 6/1998 | Zvenyatsky et al. ........ 606/206 |
| 5,827,323 A | | 10/1998 | Klieman et al. |
| 5,904,702 A | * | 5/1999 | Ek et al. ..................... 606/206 |

* cited by examiner

*Primary Examiner*—Kevin T. Truong

(57) ABSTRACT

A jaw mechanism for an endoscopic instrument is provided. The mechanism includes a drive rod having at least one boss radially protruding from a distal portion of the drive rod. A portion of the jaw mechanism has at least one groove that slidingly engages the at least one boss. A proximal portion of the drive rod is adapted to interface with an actuation mechanism. When actuated, the drive rod moves axially through a tubular member. The at least one boss travels through the at least one groove, causing the jaw mechanism to pivot around a pivot point connected to the distal portion of the tubular member.

10 Claims, 8 Drawing Sheets

JAW ASSEMBLY FOR ENDOSCOPIC INSTRUMENTS

BACKGROUND

This invention generally relates to endoscopic instruments. More particularly, the present invention provides a jaw assembly for use in an endoscopic instrument.

Laparoscopic, endoscopic, and other minimally invasive surgical techniques enable surgeons to perform fairly complicated procedures through relatively small entry points in the body. The term "laparoscopic" refers to surgical procedures performed on the interior of the abdomen, while the term "endoscopic" refers more generally to procedures performed in any portion of the body. Endoscopic surgery involves the use of an endoscope, which is an instrument permitting the visual inspection and magnification of a body cavity. The endoscope is inserted into a body cavity through a cannula extending through a hole in the soft tissue protecting the body cavity. The hole is made with a trocar, which includes a cutting instrument slidably and removably disposed within a trocar cannula. After forming the hole, the cutting instrument can be withdrawn from the trocar cannula. A surgeon can then perform diagnostic and/or therapeutic procedures at the surgical site with the aid of specialized medical instruments adapted to fit through the trocar cannula and additional trocar cannulas providing openings into the desired body cavity.

Some known advantages of minimally invasive surgical techniques include reduced trauma to the patient, reduced likelihood of infection at the surgical site, and lower overall medical costs. Accordingly, minimally invasive surgical techniques are being applied to an increasingly wider array of medical procedures.

FIG. 1 depicts a typical example of an endoscopic instrument 100. The instrument 100 may include a handle 110, a knob 120, and a tubular member 130. The handle 110 may be one of a variety of conventional configurations, such as a grip handle shown in FIG. 1. A portion of the handle 110 fits within the proximal end of the knob 120, providing an axis about which the knob 120 can be rotated. The distal end of the knob 120 may engage the proximal end of the tubular member 130, such that any rotation of the knob 120 may cause the tubular member 130 to rotate as well. The distal end of the distal member 130 may be adapted to include one of a variety of instruments or end effectors. For example, the distal end may be equipped with jaws, cutting blades, or some other instrument, depending on the desired use of the endoscopic instrument. It should therefore be appreciated that the term "jaw" is used generically in this disclosure and should be interpreted to include other types of end effectors.

FIG. 2 is a partially sectioned view of an endoscopic instrument 100. As can be appreciated, the tubular member 130 may have a lumen 135 extending from the proximal end to the distal end. A drive rod 140 may be positioned within the lumen 135. At the proximal end of the endoscopic instrument, the drive rod 140 may be attached to the handle 110. The manner in which the drive rod 140 is attached to the handle 110 depends on the handle configuration, and is well known in the art. For example, in FIG. 2, the proximal end of the drive rod 140 is formed into a ball 142 and a portion of the handle 110 has a corresponding socket 112. As is conventionally known, actuating the handle 110 moves the drive rod 140 axially within the lumen 135. This axial movement of the drive rod 140 actuates the instrument at the distal end of the tubular member 130.

FIG. 3 is a partially sectioned view of the distal end of the tubular member 130 equipped with a jaw assembly 200. The jaw assembly 200 includes two jaw members 205, which partially overlap. Each jaw member 205 has a pivot hole 210 and a substantially oval drive groove 215. Each drive groove 215 may be arranged at an angle, such that when the two jaw members 205 are aligned and fully open, the drive grooves 215 form a "V" shape. A drive pin 220 may be inserted through the drive rod 140 and rides within the drive grooves 215.

FIG. 4 is an exploded view of the distal end of the tubular member 130 and jaw assembly 200, wherein like elements bear like reference numerals. A clevis 225 is formed in the distal end of the drive rod 140. The clevis 225 may be a "U"-shaped section and at least one of the arms 227 of the "U" may have a hole 230 to accommodate a drive pin 220. The distance between the arms 227 of the clevis 225 may be slightly larger than the width of the overlapping portions of the jaw members 205. When assembled, the overlapping portions of the jaw members 205 may be placed within the clevis 225. The drive pin 220 may be inserted through the at least one hole 230 in the arm 227 of the clevis 225 and through each of the drive grooves 215. A pivot pin 235 is then inserted into a hole 240 in the distal end of the tubular member 130 and through the pivot hole 210 in each of the jaw members 205.

The jaw assembly 200 may be operated as follows. When the jaws are open, the drive pin 220 is located near one end of the drive grooves 215, for example, the end closest to the pivot pin 235. As the handle 110 is actuated, the drive rod 140 moves axially. As the drive rod 140 moves axially, the drive pin 220, which is coupled to the drive rod 140, moves axially as well. As can be appreciated, the drive pin 220 moves through the drive grooves 215 of the jaw members 205. The pivot pin 235 prevents the jaw members 205 from moving axially into the tubular member 130. Rather, as the drive pin 220 moves through the drive grooves 215, the distal ends of the jaw members 205 move toward each other and the jaw closes. As is known in the art, the axial movement may result from either a "push" or a "pull" action.

As can be appreciated, the amount of force required to close the jaws depends to a large extent on the characteristics of the material between the jaws. For example, thicker material may be more difficult to cut or compress than thinner material. As more force is exerted on the material, it is not uncommon for a portion of the clevis to fail under the stress. Typically, the point of failure occurs near where the drive pin is inserted in the clevis.

Accordingly, there is a need to provide an improved jaw assembly and drive rod configuration.

SUMMARY

In accordance with the present invention, there is an endoscopic instrument having a tubular member, a handle, and a drive rod. The tubular member has a proximal end, a distal end, and a lumen extending therethrough. The handle is coupled to the proximal end of the tubular member and has an actuating mechanism. The drive rod is disposed within the lumen of the tubular member and has a proximal end and a distal end. The proximal end of the drive rod is coupled to the actuating mechanism of the handle such that the drive rod moves axially within the lumen in response to a change in force applied to the actuating mechanism. At least one boss protrudes radially from a portion of the drive rod near the distal end of the drive rod. In addition, at least one instrument member is pivotally connected to a pivot pin. The pivot pin is coupled to the distal end of the tubular member thereby preventing axial movement of the instrument member. A portion of the at least one instrument member is adapted to slidingly engage the at least one boss.

In accordance with another aspect of the invention, the at least one instrument member is a jaw member.

In accordance with yet another aspect of the invention, there is an endoscopic instrument having a tubular member, a handle coupled to the proximal end of the tubular member, and a drive rod disposed within the lumen of the tubular member. The handle includes an actuating mechanism, and the proximal end of the drive rod is coupled to the actuating mechanism of the handle such that the drive rod moves axially within the lumen in response to a change in force applied to the actuating mechanism. At least one boss protrudes radially from a portion of the drive rod near the distal end of the drive rod. At least one jaw member is pivotally connected to a pivot pin, the pivot pin being coupled to the distal end of the tubular member thereby preventing axial movement of the jaw member. A portion of the at least one jaw member has a groove, wherein the groove slidingly engages the at least one boss.

In accordance with other aspects of the invention, a first jaw member is pivotally connected to the pivot pin and a second jaw member is fixedly connected to the distal end of the tubular member.

In accordance with yet another aspect of the invention, a first jaw member and a second jaw member are each pivotally connected to the pivot pin. A portion of each of the first jaw member and the second jaw member have a groove, wherein each groove slidingly engages a corresponding boss.

In accordance with still another aspect of the invention, each groove is open at one end.

In accordance with another aspect of the invention, each jaw member includes a stop. The stop of the first jaw member cooperates with the stop of the second jaw member to limit a range of pivotal rotation of the first jaw member and the second jaw member.

It should be emphasized that the term "comprises" or "comprising," when used in this specification, is taken to specify the presence of stated features, integers, steps, or components, but does not preclude the presence or addition of one or more other features, integers, steps, components, or groups thereof.

BRIEF DESCRIPTION OF DRAWINGS

The objects and advantages of the invention will be understood by reading the following detailed description in conjunction with the drawings in which.

DETAILED DESCRIPTION

The present invention improves upon the state of the art by providing a more reliable mechanism for actuating a jaw assembly. An improved jaw design is also provided.

Figure 1:
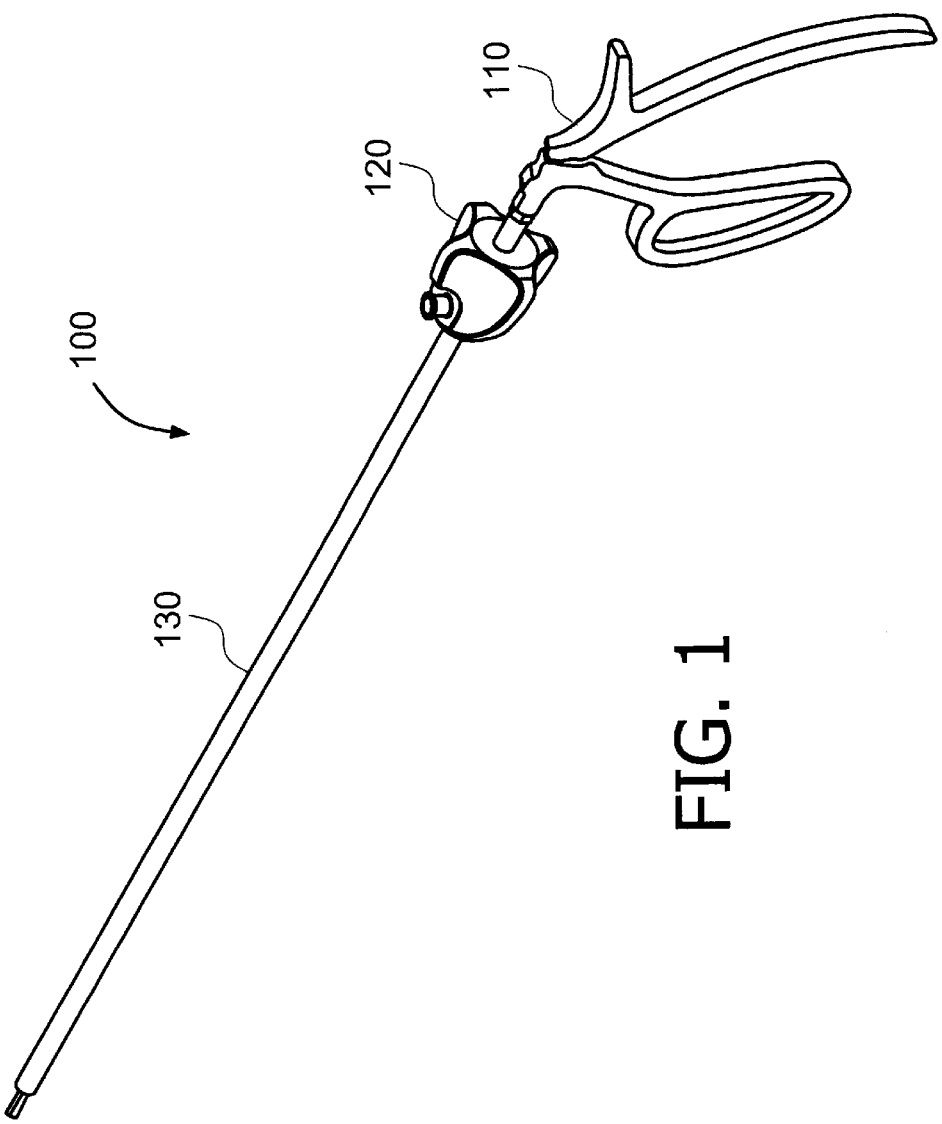
FIG. 1 is a plan view of an endoscopic instrument.
Figure 2:
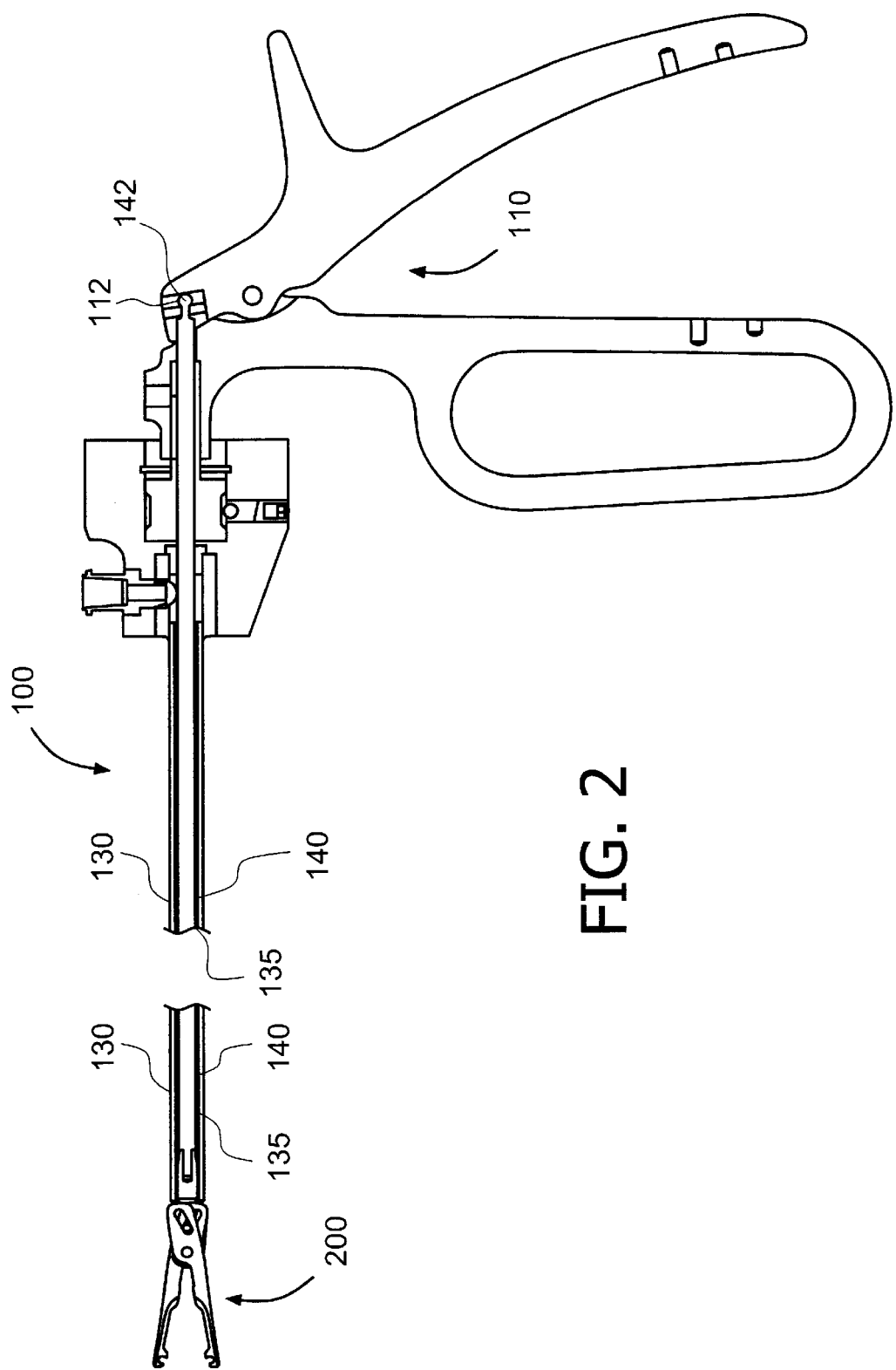
FIG. 2 is a partially sectioned view of an endoscopic instrument.
Figure 3:
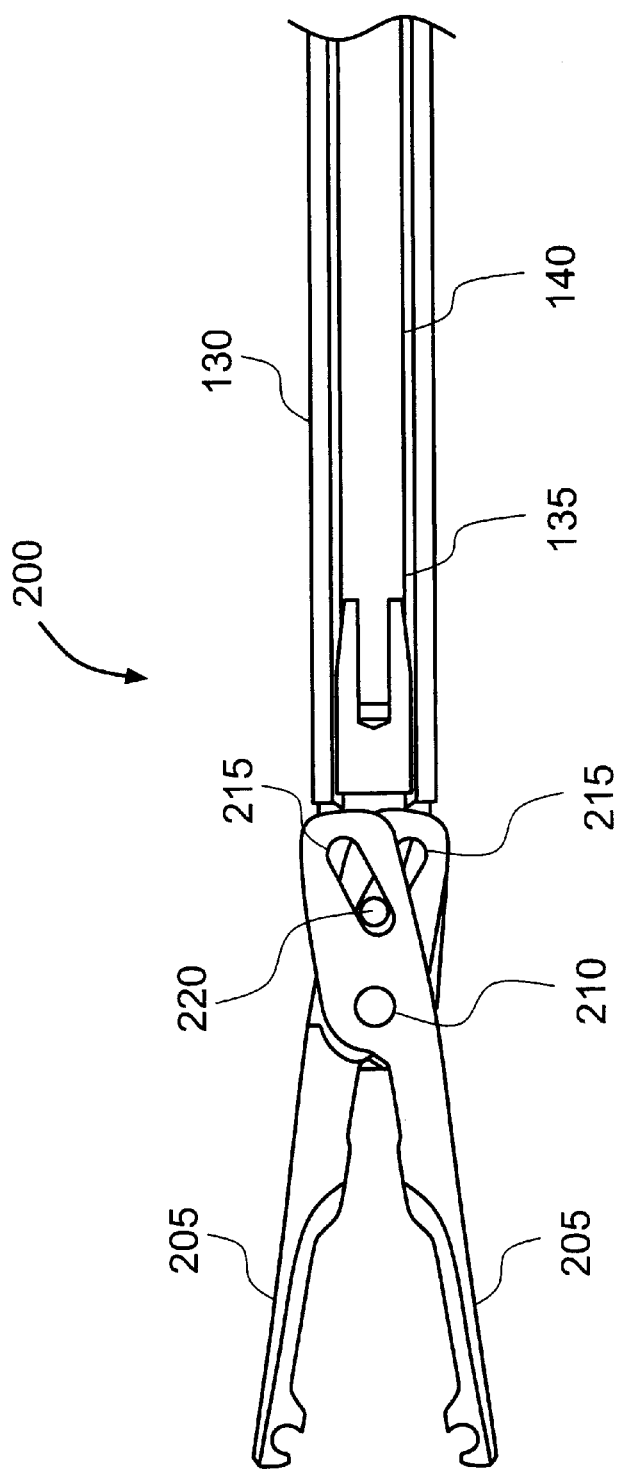
FIG. 3 is a partially sectioned view of the distal end of the tubular member equipped with a jaw assembly.
Figure 4:
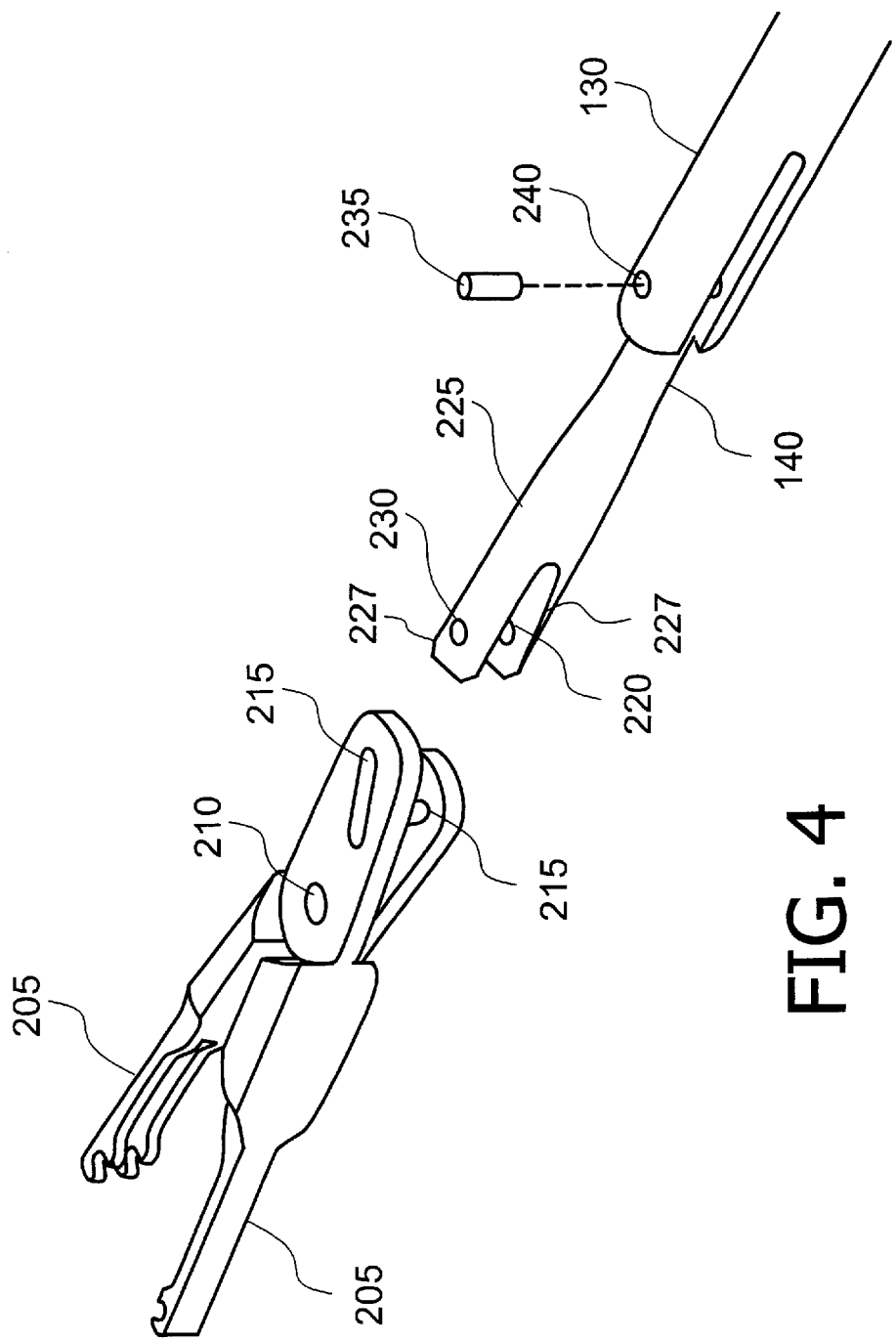
FIG. 4 is an exploded view of the distal end of the tubular member and jaw assembly.
Figure 5:
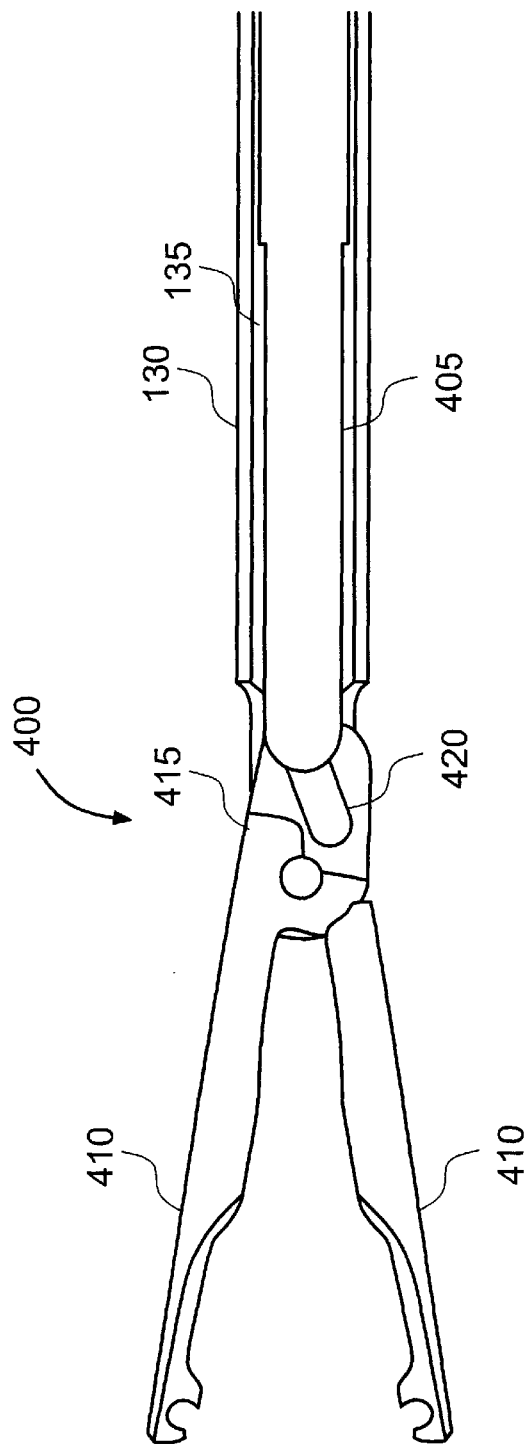
FIG. 5 is a partially sectioned view of a jaw assembly and drive rod in accordance with the invention.

FIG. 5 is a partially sectioned view of a jaw assembly 400 and drive rod 405 in accordance with the invention. It will be appreciated that the drive rod 405 and jaw assembly 400 shown in FIG. 5 replaces the drive rod 140 and jaw assembly 200 shown in FIG. 3. Thus, from the perspective of the user, the drive rod 405 and jaw assembly 400 in FIG. 5 performs the same function as the drive rod 140 and jaw assembly 200 in FIG. 3.

As shown in FIG. 5, the jaw assembly 400 includes two jaw members 410, which partially overlap. Each jaw member 410 has a pivot hole 415 and a substantially oval drive groove 420. Each drive groove 420 may be arranged at an angle, such that when the two jaw members 410 are aligned and fully open, the drive grooves 420 may form a "V" or "X" shape. As can be appreciated, the drive groove 420 may extend radially either partially or entirely through the thickness of the jaw member 410.

Figure 6:
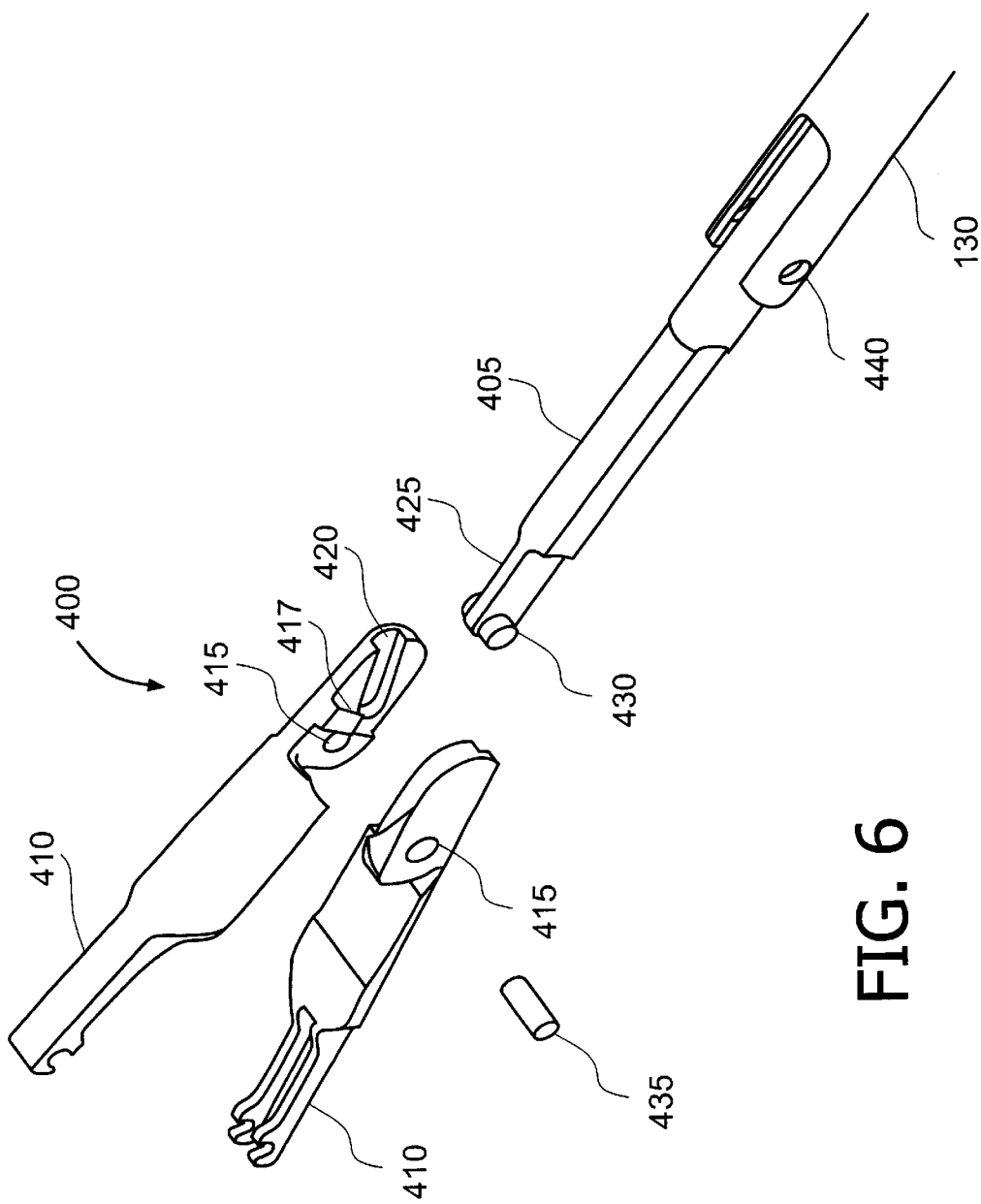
FIG. 6 is an exploded view of the jaw assembly and drive rod in accordance with the invention.

FIG. 6 is an exploded view of the jaw assembly 400 and drive rod 405, wherein like elements bear like reference numerals. As shown in FIG. 6, the distal tip of the drive rod 405 is formed into a boss bar 425. At least one boss 430 protrudes radially from the boss bar 425. When assembled, the boss bar 425 may be positioned between the proximal portions of the two jaw members 410. In this manner, each boss 430 would engage a drive groove 420 in each of the jaw members 410. The jaw assembly 400 would then be positioned partially within the tubular member 130 such that the pivot pin 435 may be inserted through a hole 440 in the tubular member 130 and the pivot hole 415 in each jaw member 410.

Figure 7:
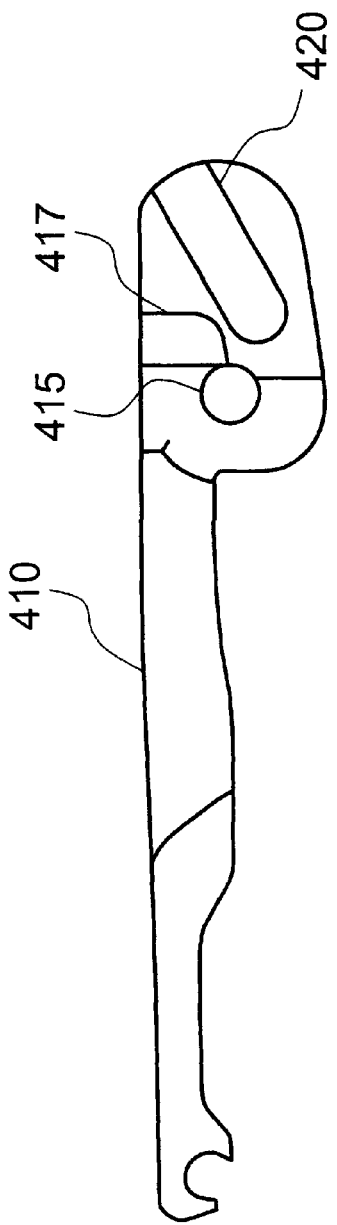
FIG. 7 is a plan view of the jaw member.

FIG. 7 is a plan view of the jaw member 410. The jaw member 410 includes the drive groove 420 and the pivot hole 415, which are discussed above. The jaw member also includes a stop 417. The stop 417 limits the distance that the jaws can open, or the "open-tip" dimension. When two jaw members 410 are arranged as shown in FIG. 5, the stop 417 of one jaw member 410 maybe in contact with the stop of the other jaw member 410. As can be appreciated, additional force maybe applied which would act to further open the jaws, such as while the endoscopic instrument is being handled or transported. In conventional devices, hyper-extending the jaw members may cause damage to portions of the instrument, such as the drive groove and components at the distal end of the drive rod. The stops 417 restrict the amount that the jaws can be hyper-extended, thus preventing damage to the drive grooves and bosses.

Figure 8:
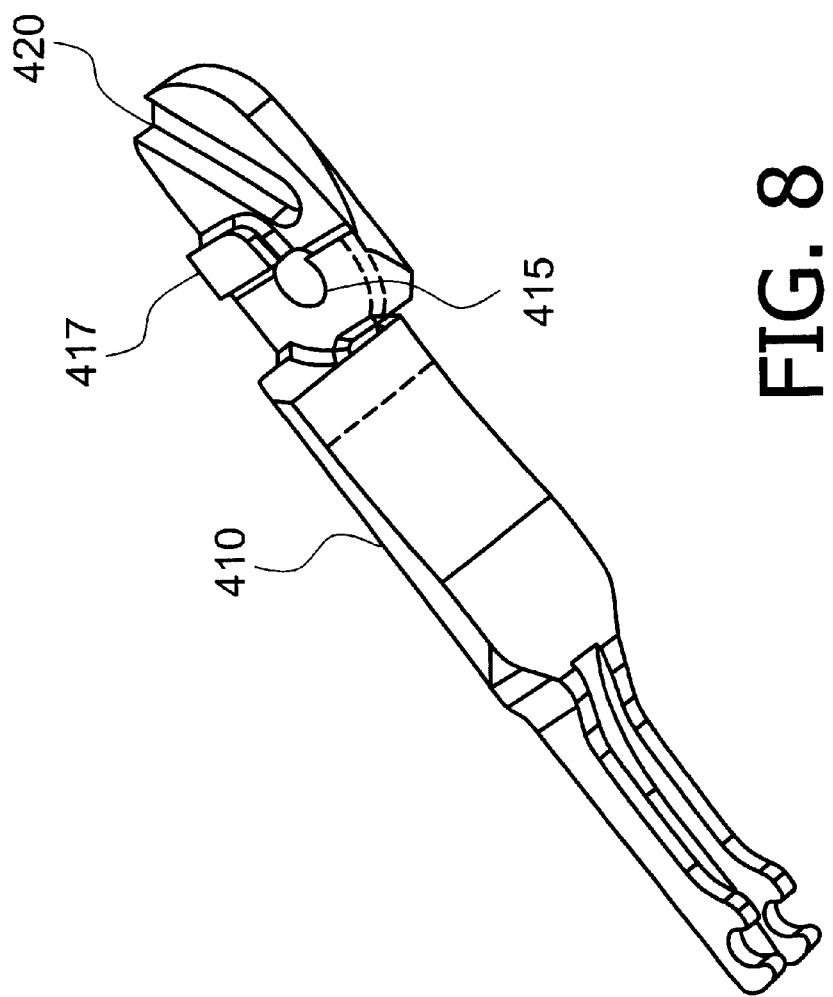
FIG. 8 is a perspective view of the jaw member.

FIG. 8 is a perspective view of the jaw member 410. As can be appreciated, the width and depth of the drive groove 420 may correspond to the diameter and height of the boss 430. The drive groove 420 may be oriented at an angle in relation to the length of the jaw member 410. For example, in relation to an axis parallel to the length of the jaw member 410 and that passed through the pivot hole 415, the proximal end of the drive groove 420 may be above the axis and the distal end of the drive groove 420 may be below the axis, resulting in the drive groove 420 having an angle of about 10° with respect to the axis. As may be appreciated, the angle of the drive groove 420 is exemplary and is not intended to limit the scope of the invention. In addition, the drive groove 420 may be substantially linear, as shown in FIG. 7, or the drive groove 420 may be curved, depending on the characteristic action desired. For example, the drive groove 420 may be curved to increase or decrease the amount of jaw closure in proportion to the distance that the drive rod moves. The proximal end of the drive groove 420 may be open, allowing for easy assembly and repair of the endoscopic instrument.

The jaw assembly 400 may be operated as follows. When the jaws are open, each boss 430 may be located near one end of the drive grooves 420, for example, the end closest to the pivot pin 435. As the handle 110 is actuated, the drive rod 405 moves axially. As the drive rod 405 moves axially, the bosses 430, which protrude from boss bar 425 portion of the drive rod 405, move axially as well. As can be appreciated, each boss 430 moves through the drive groove 420 of the respective jaw member 205. The pivot pin 435 prevents the jaw members 410 from moving axially into the tubular member 130. Rather, as the bosses 430 move through the drive grooves 420, the distal ends of the jaw members 410 move toward each other and the jaw closes. It should be noted that the length of the drive grooves 420 may be longer than necessary to accommodate the axial travel of the drive rod 405 and bosses 430. One advantage of having longer drive grooves 420 is preventing the bosses 430 from coming in contact with the ends of the drive grooves 420, or "bottoming out", and unnecessarily stressing the components of the jaw assembly 400, including the bosses 430 or material surrounding the drive grooves 420.

As can be appreciated, the exemplary embodiment of the invention eliminates the clevis and drive pin of conventional instruments. The boss-type drive rod configuration not only eliminates a typical point of failure but also reduces the number of components needed to assemble the jaw assembly portion of the endoscopic instrument.

The invention has now been described with respect to an exemplary embodiments. In light of this disclosure, those skilled in the art will likely make alternate embodiments of this invention. For example, one jaw member may be held stationary with respect to the tubular member, thereby providing for a single-boss embodiment. These and other alternate embodiments are intended to fall within the scope of the claims which follow.

What is claimed is:

1. An endoscopic instrument comprising:
   a tubular member having a proximal end, a distal end, and a lumen extending therethrough;
   a handle coupled to the proximal end of the tubular member, the handle having an actuating mechanism;
   a drive rod disposed within the lumen of the tubular member, the drive rod having a proximal end and a distal end, the proximal end of the drive rod being coupled to the actuating mechanism of the handle such that the drive rod moves axially within the lumen in response to a change in force applied to the actuating mechanism;
   at least one boss protruding radially from a portion of the drive rod near the distal end of the drive rod; and
   at least one instrument member pivotally connected to a pivot pin, the pivot pin being coupled to the distal end of the tubular member thereby preventing axial movement, a portion of the at least one instrument member being adapted to slidingly engage the at least one boss.

2. The instrument of claim 1, wherein the at least one instrument member is a jaw member.

3. An endoscopic instrument comprising:
   a tubular member having a proximal end, a distal end, and a lumen extending therethrough;
   a handle coupled to the proximal end of the tubular member, the handle having an actuating mechanism;
   a drive rod disposed within the lumen of the tubular member, the drive rod having a proximal end and a distal end, the proximal end of the drive rod being coupled to the actuating mechanism of the handle such that the drive rod moves axially within the lumen in response to a change in force applied to the actuating mechanism;
   at least one boss protruding radially from a portion of the drive rod near the distal end of the drive rod; and
   at least one jaw member pivotally connected to a pivot pin, the pivot pin being coupled to the distal end of the tubular member thereby preventing axial movement, a portion of the at least one jaw member having a groove, wherein the groove slidingly engages the at least one boss.

4. The instrument of claim 3, wherein a first jaw member is pivotally connected to the pivot pin and a second jaw member is fixedly connected to the distal end of the tubular member.

5. The instrument of claim 3, wherein a first jaw member and a second jaw member are each pivotally connected to the pivot pin, a portion of each of the first jaw member and the second jaw member having a groove, wherein each groove slidingly engages a corresponding boss.

6. The instrument of claim 5, wherein each groove is open at one end.

7. The instrument of claim 3, wherein each jaw member includes a stop, the stop of the first jaw member cooperating with the stop of the second jaw member to limit a range of pivotal rotation of the first jaw member and the second jaw member.

8. The endoscopic instrument of claim 3, wherein at least a portion of the groove of the at least one jaw member extends proximal to the pivot pin.

9. An endoscopic instrument comprising:
   a tubular member having a proximal end, a distal end, and a lumen extending therethrough;
   a handle coupled to the proximal end of the tubular member, the handle having an actuating mechanism;
   a drive rod disposed within the lumen of the tubular member, the drive rod having a proximal end and a distal end, the proximal end of the drive rod being coupled to the actuating mechanism of the handle such that the drive rod moves axially within the lumen in response to a change in force applied to the actuating mechanism;
   at least one boss protruding radially from a portion of the drive rod near the distal end of the drive rod; and
   at least one jaw member at least partially disposed within the distal end of the tubular member, the at least one jaw member pivotally engaging a pivot pin, the pivot pin being inserted through a hole in at least one side of the distal end of the tubular member thereby preventing axial movement of the at least one jaw member, a portion of the at least one jaw member having a groove, wherein the groove slidingly engages the at least one boss.

10. The endoscopic instrument of claim 8, wherein at least a portion of the groove of the at least one jaw member extends proximal to the pivot pin.

* * * * *

UNITED STATES PATENT AND TRADEMARK OFFICE
CERTIFICATE OF CORRECTION

PATENT NO. : 6,733,514 B2
DATED : May 11, 2004
INVENTOR(S) : John D. Miser

It is certified that error appears in the above-identified patent and that said Letters Patent is hereby corrected as shown below:

Column 5,
Line 55, replace "at least one" with -- a first and second --; and
Line 56, after the second occurrence of "drive rod", insert -- and along a same axis of the drive rod --.

Column 6,
Line 11, replace "at least one" with -- a first and second --;
Line 12, after the second occurrence of "drive rod", insert -- and along a same axis of the drive rod --;
Line 32, before the first occurrence of "stop" , insert -- protruding --;
Line 35, after "member", insert -- in the open position --.
Line 52, replace "at least one" with -- a first and second --; and
Line 53, after the second occurrence of "drive rod", insert -- and along a same axis of the drive rod --.
Line 63, replace "claim 8" with -- claim 9 --.

Signed and Sealed this

Fourth Day of January, 2005

JON W. DUDAS
*Director of the United States Patent and Trademark Office*